United States Patent
Consoli et al.

(10) Patent No.: US 11,160,737 B2
(45) Date of Patent: Nov. 2, 2021

(54) KERATIN FIBER DYEING COMPOSITION

(71) Applicant: BEAUTY & BUSINESS S.p.A., Milan (IT)

(72) Inventors: Antonio Consoli, Urgnano (IT); Katiuscia Grevalcuore, Bergamo (IT); Massimo Fabbi, Mozzo (IT); Emanuela Facchetti, Romano di Lombardia (IT)

(73) Assignee: BEAUTY & BUSINESS S.p.A., Milan (IT)

( * ) Notice: Subject to any disclaimer, the term of this patent is extended or adjusted under 35 U.S.C. 154(b) by 0 days.

(21) Appl. No.: 17/094,921

(22) Filed: Nov. 11, 2020

(65) Prior Publication Data
US 2021/0145718 A1 May 20, 2021

(30) Foreign Application Priority Data
Nov. 15, 2019 (IT) .................. 102019000021273

(51) Int. Cl.
| | | |
|---|---|---|
| *A61Q 5/10* | (2006.01) | |
| *A61K 8/41* | (2006.01) | |
| *A61K 8/02* | (2006.01) | |
| *A61K 8/04* | (2006.01) | |
| *A61K 8/362* | (2006.01) | |
| *A61Q 5/06* | (2006.01) | |

(52) U.S. Cl.
CPC .............. *A61K 8/41* (2013.01); *A61K 8/0216* (2013.01); *A61K 8/042* (2013.01); *A61K 8/362* (2013.01); *A61Q 5/065* (2013.01); *A61K 2800/432* (2013.01)

(58) Field of Classification Search
CPC . A61Q 5/10; A61K 8/22; A61K 8/411; A61K 8/4926; A61K 8/415; A61K 8/41; A61K 8/347; A61K 8/37; A61K 8/042; A61K 8/0216; A61K 8/362
See application file for complete search history.

(56) References Cited

U.S. PATENT DOCUMENTS

| | | | | |
|---|---|---|---|---|
| 7,150,868 | B2 * | 12/2006 | Ohta ................. | A61K 8/37 424/70.1 |
| 2005/0097684 | A1 * | 5/2005 | Narasimhan ........... | A61Q 5/10 8/405 |
| 2007/0157399 | A1 * | 7/2007 | Nobuto ................ | A61K 8/466 8/405 |
| 2014/0353200 | A1 * | 12/2014 | Samain ............... | A61K 8/37 206/524.1 |
| 2015/0082555 | A1 * | 3/2015 | Rapold ............... | A61Q 5/10 8/416 |
| 2015/0374601 | A1 * | 12/2015 | Sabelle .............. | A61K 8/494 8/409 |
| 2016/0158130 | A1 * | 6/2016 | Mori ................. | A61K 8/411 8/435 |

FOREIGN PATENT DOCUMENTS

| | | | |
|---|---|---|---|
| EP | 3427720 | * | 1/2019 |
| EP | 3427720 A1 | | 1/2019 |

OTHER PUBLICATIONS

Search Report and Written Opinion of Priority Document IT201900021273 dated Jun. 19, 2020.

* cited by examiner

*Primary Examiner* — Eisa B Elhilo
(74) *Attorney, Agent, or Firm* — Silvia Salvadori, P.C.; Silvia Salvadori

(57) ABSTRACT

Disclosed are hair-colouring compositions comprising an oxidative dye and an alkalising agent consisting of isopropanolamine and a malic acid diester. The compositions according to the invention, due to synergic effects between isopropanolamine and the malic acid diester, are advantageous, because they lighten the hair by up to four levels, do not have an unpleasant odour, and limit the damage caused to the hair, maintaining its integrity and consequently its natural characteristics of elasticity, shine and combability.

7 Claims, No Drawings

KERATIN FIBER DYEING COMPOSITION

This U.S. Non-Provisional Application claims priority to and the benefit from Italian Patent Application No. 102019000021273 filed on Nov. 15, 2019, the content of which is incorporated herein by reference in its entirety.

The present invention relates to the cosmetics industry in general and the hair-dyeing sector in particular.

PRIOR ART

Among the various types of hair-colouring compositions, oxidative dyes are particularly important due to their long duration. They are usually stable for a very long time, ranging from 4 to 8 weeks under normal conditions, and are therefore called "permanent" dyes.

The oxidative system is based on the reaction of primary intermediates with couplers; both types of molecule are colourless. In the presence of air or oxidants such as hydrogen peroxide, primary dyes, which are primary aromatic amines with an additional hydroxyl or amino group, substituted or not substituted, in the para or ortho position, react with resorcinol, m-aminophenol, m-phenylenediamine or 1-naphthol couplers.

As the dye molecules thus formed in the cuticle are larger than the starting primary intermediates and the highly diffusible couplers, they remain trapped inside the hair, and there is therefore no significant fading due to successive washes or the action of external agents.

In order to be effective, oxidative dyes also require the presence of an alkalising compound.

Historically, the most commonly used alkalising agent has been ammonia. Said compound is highly volatile, and has an unpleasant pungent odour. To eliminate this drawback, ammonia-free hair-colouring preparations containing monoethanolamine (MEA) have become widely used in the last 20 years. Said alkalising agent is not very volatile, and is not completely removed from the hair by shampoo. For this reason, dye after dye it accumulates on the hair fiber, making the hair fragile, opaque and inelastic. (Comparison of damage to human hair fibers caused by monoethanolamine- and ammonia-based hair colorants J. Cosmet. Sci. 65, 1-9; WO 2017109132).

US2019117541 describes an alternative alkalising system that solves said problems, comprising a basic amino acid (preferably arginine) and a fatty acid ester with glycerol polyethoxylate (preferably PEG-90 glyceryl isostearate).

Said alkalising system has the advantage of not having an unpleasant odour and not damaging the hair fiber, while guaranteeing excellent results in terms of shine, combability and elasticity, but presents the drawback of not lightening the hair. Only tone-on-tone colouring can be achieved with said alkalising agent, not colouring with lightening by up to 4 levels as is the case with ammonia or monoethanolamine.

In the past, the hair was mainly dyed to conceal areas of white hair, whereas there is now increased demand for fashionable hair colours as an expression of the personality. Absence of lightening considerably limits the choice of shades by customers, as they cannot change from brown to blonde, for example.

There is consequently a need for a novel alkalising agent able to lighten the hair by up to four levels, which does not have an unpleasant odour, and limits damage to the hair by maintaining its integrity, and consequently its natural characteristics of elasticity, shine and combability.

DESCRIPTION OF THE INVENTION

It has now been discovered that isopropanolamine (MIPA) represents an advantageous alternative to monoethanolamine (MEA) as an alkalising agent in oxidative hair dyes, especially as regards the impact on the integrity of the hair structure. Although MIPA has a chemical structure similar to that of MEA, it damages the hair far less, while maintaining a similar performance in terms of covering white hair.

MIPA is not odourless, but its characteristic odour can easily be masked with a fragrance.

The hair lightening generated is slightly less than that obtainable with MEA, but it has been found that the combination of MIPA with a malic acid diester enhances lightening until a lightening level comparable to or even greater than that obtained with monoethanolamine.

The synergy between malic acid diester and MIPA can even partly remove cosmetic colour (the colour generated by an oxidative or direct hair dye) from the hair. Total or partial removal of cosmetic colour is particularly useful when the colour of previously dyed hair is to be changed. The combination of MIPA with a malic acid diester also improves the coverage of white hair by completely colouring it, therefore achieving better coverage than a hair-colouring composition containing MEA. The malic acid diester can be, for example, diisostearyl malate, di-C12-13 alkyl malate, diethylhexyl malate, diisoamyl malate, dibutyloctyl malate, dioctyldodecyl malate, diglyceryl stearate malate, diglyceryl ether malate or glyceryl stearate/malate.

The preferred malic acid diesters according to the invention are diisostearyl malate and di-C12-13 alkyl malate.

Diisostearyl malate is conventionally used as an emollient in cosmetic products, mainly in the skin-care and make-up fields, and is described for that use by various manufacturers, such as Sabo Spa (saboderm DISM); Corum (corum 5015), Kokyu Alcohol Kogyo Co., LTD (haimalate DIS).

Diisostearyl malate is not generally used in the hair-care field, with some exceptions, such as the after-colour conditioner present in the Revlon Color Silk kit (also described in U.S. Pat. No. 7,166,137).

Also di-C12-13 alkyl malate is an emollient, which is used in the hair-care field as a conditioning agent. It is described for that use by manufacturer Sasol, for example, which markets it under the name of Cosmacol Emi.

The subject of the invention is therefore hair-colouring compositions comprising an oxidative dye and an alkalising agent consisting of isopropanolamine and a malic acid diester. The compositions according to the invention comprise 0.1 to 10% by weight of isopropanolamine, and 0.1 to 20% by weight of malic acid diester.

The compositions can comprise two or more components, at least one of which is an activator, to be mixed before use.

The alkalising system constituted by the combination of MIPA and malic acid diester, in particular diisostearyl malate, produces a better result in terms of lightening, odour and hair damage than the other alkalinising agents alternative to MEA already used on the market, such as aminomethyl propanol (AMP), present in Pravana ChromaSilk ColourLush and Paul Mitchel The Demi, dimethylamino methylpropanol (DMAMP), present in Mineral Colours by Rodolphie & Co, and ammonium carbonate, present in Perfect 10 by Clairol.

Definitions

The colour "level" or "height of tone" indicates the depth of the colour, ie. how light or dark it is. The ICC (International Colour Chart) system uses numbers to define the depth of colour. Said values range from 1 to 11, wherein 1 denotes the darkest shade (black) and 11 the lightest (platinum blonde).

Table A shows the usual names matching each number.

TABLE A

| Level | Level name |
|---|---|
| 1 | Black |
| 2 | Very dark brown |
| 3 | Dark brown |
| 4 | Medium brown |
| 5 | Light brown |
| 6 | Dark blonde |
| 7 | Medium blonde |
| 8 | Light blonde |
| 9 | Very light blonde |
| 10 | Lightest blonde |
| 11 | Platinum blonde |

"Lightening" is therefore defined as the change from one level to a lighter one by means of chemical treatment of the keratin fiber.

A dye that does not produce lightening is called "tone on tone".

"Elasticity" means the extent of the rigidity of the keratin fiber. It is a mechanical property defined by the ratio between the strength applied and the elongation of the fiber. The measurement is conducted with a dynamometer (e.g. DIA-STRON MTT670). The reference parameter is the modulus of elasticity (Young's Modulus). The higher said parameter, the better the elasticity of the hair, and consequently its health.

"Combability" means the amount of work required to comb locks of hair. The measurement is conducted with a dynamometer (e.g. DIA-STRON MTT175). The less work required, the greater the combability.

Light interacts with hair fibers. When incident light is reflected on the surface of the fibers, a glossy band is created on the hair which is called "shine". This parameter is measurable with an instrument designed by Bossanova Technologies, called the SAMBA Hair system.

"Integrity" means the extent of erosion of the keratin fiber. Detailed images of the hair cuticles can be obtained with a scanning electron microscope (SEM). ImageJ software provides a method of measuring the distance between cuticles. The shorter the cuticles, the healthier the hair. On damaged hair, the cuticle has been removed (eroded) by treatment (such as a dye), and the distance between the remaining layers of cuticle is longer.

"Alkalising agent" or "alkaliser" means an ingredient or combination of ingredients able to adjust the pH of the cosmetic composition to a value above 7.

"Neutralising agent" or "neutraliser" means an ingredient able to neutralise acid ingredients present in the formulation, by adjusting the pH of the composition from a value below 7 to a neutral pH.

Examples of neutralising agents are sodium hydroxide, potassium hydroxide, urea, allantoin, tripotassium phosphate, sodium saccharine, and combinations thereof.

"Activator" means an agent able to promote the oxidation and coupling reaction between primary dyes and couplers.

Examples of activators include hydrogen peroxide, carbamide peroxide, perborates and persulphates or peracids, preferably hydrogen peroxide. The amount of activator, if present, can range from 0.1 to 50% by weight of the ready-to-use mixture.

DETAILED DESCRIPTION OF THE INVENTION

The composition according to the invention is an oxidative hair dyeing composition with up to 4 levels of lightening or tone on tone, comprising an oxidative dye and an alkalising agent consisting of isopropanolamine and a malic acid diester.

The composition according to the invention can be in "ready-to-use" form, comprising two or more ingredients designed to be mixed before use. Alternatively, it can be applied directly to the hair, in which case the activator is the oxygen present in the air (progressive dye).

Depending on their composition, ready-to-use hair-colouring preparations can be weakly acidic, neutral or alkaline, and have a pH ranging from about 3 to 11, preferably from 6.5 to 11.

The hair-colouring composition according to the invention can be in cream, gel, foam, liquid or solid form.

The composition according to the invention must also contain at least one oxidative dye. The preferred dyes are listed below according to the INCI nomenclature (International Nomenclature of Cosmetic Ingredients):

1-Acetoxy-2-Methylnaphthalene, 5-Amino-6-Chloro-o-Cresol, 5-Amino-4-Chloro-o-Cresol, 4-Amino-m-Cresol, 6-Amino-m-Cresol, 3-Amino-2,4-Dichlorophenol, 6-Amino-2,4-Dichloro-m-Cresol, 3-Amino-2,4-Dichlorophenol, 5-Amino-2,6-Dimethoxy-3-Hydroxypyridine, 5-Amino-2,6-Dimethoxy-3-Hydroxypyridine, 3-Amino-2,6-Dimethylphenol, 2-Amino-5-Ethylphenol, 5-Amino-4-Fluoro-2-Methylphenol Sulphate, 2-Amino-4-Hydroxyethylaminoanisole, 2-Amino-4-Hydroxyethylaminoanisole, 2-Amino-3-Hydroxypyridine, 4-Amino-2-Hydroxytoluene, 2-Aminomethyl-p-Aminophenol, 4-Amino-2-Nitrodiphenylamine-2'-Carboxylic Acid, m-Aminophenol, o-Aminophenol, p-Aminophenol, 1,3-Bis-(2,4-Diaminophenoxy) propane, 4,6-Bis(2-Hydroxyethoxy)-m-Phenylenediamine, 2,6-Bis(2-Hydroxyethoxy)-3,5-Pyridinediamine, N,N-Bis (2-Hydroxyethyl)-p-Phenylenediamine, 4-Chloro-2-Aminophenol, 2-Chloro-p-Phenylenediamine, 4-Chlororesorcinol, N-Cyclopentyl-m-Aminophenol, 3,4-Diaminobenzoic Acid, 4,5-Diamino-1-((4-Chlorophenyl)Methyl)-1H-Pyrazole-Sulphate, 2,3-Diaminodihydro-pyrazolo Pyrazolone Dimethosulphonate, 2,4-Diaminodiphenylamine, 4,4'-Diaminodiphenylamine, 2,4-Diamino-5-Methylphenetole, 2,4-Diamino-5-Methylphenoxyethanol, 4,5-Diamino-1-Methylpyrazole, 2,4-Diaminophenol 2,4-Diaminophenoxyethanol, 2,6-Diaminopyridine, 2,6-Diamino-3-((Pyridin-3-yl)Azo)Pyridine, N,N-Diethyl-m-Aminophenol, N,N-Diethyl-p-Phenylenediamine, N,N-Diethyltoluene-2,5-Diamine, 2,6-Dihydroxy-3,4-Dimethylpyridine, 2,6-Dihydroxyethylaminotoluene, Dihydroxyindole, Dihydroxyindoline, 2,6-Dimethoxy-3,5-Pyridinediamine, m-Dimethylaminophenyl Urea, N,N-Dimethyl-p-Phenylenediamine, 2,6-Dimethyl-p-Phenylenediamine, N,N-Dimethyl 2,6-Pyridinediamine, 4-Ethoxy-m-Phenylenediamine, 3-Ethylamino-p-Cresol, 4-Fluoro-6-Methyl-m-Phenylenediamine, 1-Hexyl 4,5-Diamino Pyrazole Sulphate, Hydroquinone, Hydroxyanthraquinoneaminopropyl Methyl Morpholinium Methosulphate, Hydroxybenzomorpholine, Hydroxyethoxy Aminopyrazolopyridine, Hydroxyethylaminomethyl-p-Aminophenol, 1-Hydroxyethyl 4,5-Diamino Pyrazole, Hydroxyethyl-2,6-Dinitro-p-Anisidine, Hydroxyethyl-3,4-Methylenedioxyaniline, Hydroxyethyl-p-Phenylenediamine, 2-Hydroxyethyl Picramic Acid, 6-Hydroxyindole, Hydroxypropyl Bis(N-Hydroxyethyl-p-Phenylenediamine), Hydroxypropyl-p-

Phenylenediamine, Hydroxypyridinone, Isatin, N-Isopropyl 4,5-Diamino Pyrazole, N-Methoxyethyl-p-Phenylenediamine, 6-Methoxy-2-methylamino-3-aminopyridine, 2-Methoxymethyl-p-Aminophenol, 2-Methoxy-methyl-p-Phenylenediamine, 2-Methoxy-p-Phenylenediamine, 6-Methoxy-2,3-Pyridinediamine, 4-Methoxytoluene-2,5-Diamine, p-Methylaminophenol, 4-Methylbenzyl 4,5-Diamino Pyrazole, 2,2'-Methylenebis 4-Aminophenol, 3,4-Methylenedioxyaniline, 3,4-Methylenedioxyphenol, 2-Methyl-5-Hydroxyethylaminophenol, Methylimidazoliumpropyl p-Phenylenediamine, 2-Methyl-1-Naphthol, 2-Methylresorcinol, 1,5-Naphthalenediol, 1,7-Naphthalenediol, 2,3-Naphthalenediol, 2,7-Naphthalenediol, 1-Naphthol, 2-Naphthol, PEG-3 2,2'-Di-p-Phenylenediamine, p-Phenetidine, m-Phenylenediamine, p-Phenylenediamine, Phenyl Methyl Pyrazolone, N-Phenyl-p-Phenylenediamine, Picramic Acid, Pyrocatechol, Pyrogallol, Resorcinol, Sodium Picramate, Tetraaminopyrimidine, Tetrahydro-6-Nitroquinoxaline, Tetrahydropyranyl, Resorcinol, Toluene-2,5-Diamine, Toluene-2,6-Diamine, Toluene-3,4-Diamine, 2,5,6-Triamino-4-Pyrimidinol, 1,2,4-Trihydroxybenzene.

The oxidative dyes can be in the form of salts.

The total amount of the combination of primary dyes and couplers in the hair-colouring preparation according to the invention preferably ranges from about 0.001 to 20% by weight, preferably from about 0.01 to 6.0% by weight of the weight of the composition.

The hair-colouring preparations according to the invention can also contain direct dyes. Examples of direct dyes, defined according to the INCI nomenclature (European Community Decision 2006/257/EC as amended—International Nomenclature of Cosmetic Ingredients), include:

Acid green 25, Acid blue 74, Acid blue 3, Acid blue 9, Acid red 18, Acid red 184, Acid red 195, Acid red 27, Acid red 33, Acid red 35, Acid red 51, Acid red 73, Acid red 87, Acid red 92, Acid red 95, Acid violet 43, Acid violet 9, Acid yellow 23, Acid yellow 3, Acid yellow 36, Acid yellow 73, Acid orange 6, Acid orange 7, Acid green 1, Acid green 50, Acid Blue 1, Acid Blue 62, Acid Brown 13, Acid Orange 3, Acid Orange 24, Acid Red 14, Acid Red 35, Acid Red 52, Acid Yellow 1, 2-Amino-6-Chloro-4-Nitrophenol, 4-Amino-2-Nitrodiphenylamine-2'-Carboxylic Acid, 2-Amino-3-Nitrophenol, 2-Amino-4-Nitrophenol, 2-Amino-5-Nitrophenol, 4-Amino-2-Nitrophenol, 4-Amino-3-Nitrophenol, Basic Blue 3, Basic Blue 7, Basic Blue 9, Basic Blue 26, Basic Blue 47, Basic Blue 75, Basic Blue 99, Basic Blue 124, Basic Brown 4, Basic Brown 16, Basic Brown 17, Basic Green 1, Basic Green 4, Basic Orange 1, Basic Orange 2, Basic Orange 31, Basic Red 1, Basic Red 1:1, Basic Red 2, Basic Red 22, Basic Red 46, Basic Red 51, Basic Red 76, Basic Red 118, Basic Violet 1, Basic Violet 2, Basic Violet 3, Basic Violet 4, Basic Violet 10, Basic Violet 11:1, Basic Violet 14, Basic Violet 16, Basic Yellow 28, Basic Yellow 40, Basic Yellow 57, Basic Yellow 87, N,N'-Bis(2-Hydroxyethyl)-2-Nitro-p-Phenylenediamine, 2-Chloro-6-Ethylamino-4-Nitrophenol, 2-Chloro-5-Nitro-N-Hydroxyethyl p-Phenylenediamine, N,N'-Dimethyl-N-Hydroxyethyl-3-Nitro-p-Phenylenediamine, Direct Black 51, Direct Red 23, Direct Red 80, Direct Red 81, Direct Violet 48, Direct Yellow 12, Disperse Black 9, Disperse Blue 1, Disperse Blue 3, Disperse Blue 7, Disperse Blue 377, Disperse Brown 1, Disperse Orange 3, Disperse Red 11, Disperse Red 15, Disperse Red 17, Disperse Violet 1, Disperse Violet 4, Disperse Violet 15, HC Blue No. 2, HC Blue No. 4, HC Blue No. 5, HC Blue No. 6, HC Blue No. 8, HC Blue No. 9, HC Blue No. 10, HC Blue No. 11, HC Blue No. 12, HC Blue No. 13, HC Blue No. 14, HC Blue No. 15, HC Blue No. 16, HC Blue No. 17, HC Blue No. 18, HC Brown No. 1, HC Brown No. 2, HC Green No. 1, HC Orange No. 1, HC Orange No. 2, HC Orange No. 3, HC Orange No. 5, HC Orange No. 6, HC Red No. 1, HC Red No. 3, HC Red No. 7, HC Red No. 8, HC Red No. 9, HC Red No. 10, HC Red No. 11, HC Red No. 13, HC Red No. 14, HC Red No. 15, HC Red No. 17, HC Red No. 18, HC Violet No. 1, HC Violet No. 2, HC Yellow No. 2, HC Yellow No. 4, HC Yellow No. 5, HC Yellow No. 6, HC Yellow No. 7, HC Yellow No. 8, HC Yellow No. 9, HC Yellow No. 10, HC Yellow No. 11, HC Yellow No. 12, HC Yellow No. 13, HC Yellow No. 14, HC Yellow No. 15, HC Yellow No. 16, HC Yellow No. 17, 2-Hydroxyethylamino-5-Nitroanisole, Hydroxyethyl-2-Nitro-p-Toluidine, 4-Hydroxypropylamino-3-Nitrophenol, 3-Methylamino-4-Nitrophenoxyethanol, 3-Nitro-4-Aminophenoxyethanol, 3-Nitro-p-Cresol, 2-Nitro-5-Glyceryl Methylaniline, 4-Nitroguaiacol, 3-Nitro-p-Hydroxyethylaminophenol, 2-Nitro-N-Hydroxyethyl-p-Anisidine, Nitrophenol, 4-Nitrophenyl Aminoethylurea, 4-Nitro-o-Phenylenediamine, 4-Nitro-m-Phenylenediamine, 4-Nitro-o-Phenylenediamine, 2-Nitro-p-Phenylenediamine, 6-Nitro-2,5-Pyridinediamine, 6-Nitro-o-Toluidine, Pigment Blue 15, Pigment Blue 15:1, Pigment Violet 23, Pigment Yellow 13, Solvent Black 3, Solvent Black 5, Solvent Blue 35, Solvent Yellow 85, Solvent Yellow 172, Tetrabromophenol Blue, Tetrahydro-6-Nitroquinoxaline, Tetrahydropyranyl Resorcinol.

The hair-colouring preparations according to the invention can also contain one or more natural or synthetic additives commonly used in the cosmetics industry.

Examples of said additives comprise solvents such as water, low-molecular-weight aliphatic mono- or polyalcohols, esters and ethers thereof, for example alkanols, in particular having 1 to 4 carbon atoms, such as ethanol, n-propanol, isopropanol, butanol and isobutanol; bivalent or trivalent alcohols, in particular having 2 to 6 carbon atoms, such as ethylene glycol, propylene glycol, 1,3-propanediol, 1,4-butanediol, 1,5-pentanediol, 1,6-hexanediol, 1,2,6-hexanetriol, glycerin, diethylene glycol, dipropylene glycol, polyalkylene glycols, such as triethylene glycol, polyethylene glycol, tripropylene glycol and polypropylene glycol; low-molecular-weight alkyl ethers of multivalent alcohols, such as ethylene glycol monomethyl ether, ethylene glycol monoethyl ether, ethylene glycol monopropyl ether or ethylene glycol monobutyl ether, diethylene glycol monomethyl ether or diethylene glycol monoethyl ether, triethylene glycol monomethyl ether or triethylene glycol monoethyl ether; ketones and keto alcohols, in particular having 3 to 7 carbon atoms, such as acetone, methyl ethyl ketone, diethyl ketone, methyl isobutyl ketone, methyl phenyl ketone, cyclopentanone, cyclohexanone and diacetone alcohol; ethers such as dibutyl ether, tetrahydrofuran, dioxane or diisopropylether; esters such as ethyl formate, methyl formate, methyl acetate, ethyl acetate, propyl acetate, butyl acetate, phenyl acetate, ethylene glycol monoethyl ether acetate or acetic acid hydroxyethyl ester; amides such as N-methylpyrrolidone; and urea, tetramethyl urea and thiodiglycol.

The following can also be present: anionic, cationic, non-ionic, amphoteric or zwitterionic emulsifiers; wetting agents; surfactants, such as fatty alcohol sulphates, alkylsulphonates, alkylbenzene sulphonates, alklymethyl ammonium salts, alkylbetaine, α-olefin sulphonates, ethoxylated fatty alcohols, ethoxylated nonylphenols, fatty acid alkanolamines, ethoxylated esters of fatty acids, polyglycol ether sulphates of fatty acids and alkylpolyglycosides, thickeners, such as higher fatty alcohols, starches, cellulose derivatives, vaseline, paraffin oil, fatty acids and other fatty ingredients in emulsified form, water-soluble polymer thickeners, such as natural gums, guar gum, tara gum, xanthan gum, carob flour, pectin, dextran, agar-agar, amylose, amylopectin, dextrin, synthetic clays or hydrocolloids, such as polyvinyl alcohol; conditioning and restructuring agents such as lanolin derivatives, cholesterol, pantothenic acid, water-soluble cationic polymers, protein derivatives, amino acids, provitamins, vitamins, plant extracts, sugar and betaine; auxiliary agents such as electrolytes, antioxidants, fatty amides, sequestering agents, film-forming agents and preservatives, as well as beeswax.

The addition to the hair-colouring preparations according to the invention of non-ionic and/or anionic surfactants such as fatty alcohol sulphates, in particular lauryl sulphate or sodium cocoyl sulphate; ethoxylated fatty alcohol sulphates, in particular sodium lauryl ether sulphates with 2 to 4 molecular units of ethylene oxide, ethoxylated esters of fatty acids, ethoxylated nonylphenols, ethoxylated fatty alcohols, alkylbenzene sulphonates or alkanolamides of fatty acids, in a total quantity preferably ranging from about 0.1 to 30% by weight, more preferably from 0.2 to 15% by weight, can be particularly advantageous.

Examples of useful cationic surfactants are quaternary ammonium compounds; ammonium halides such as alkyltrimethylammonium chlorides, dialkyldimethylammonium chlorides and trialkylmethylammonium chlorides. Specific examples are cetyltrimethylammonium chloride, stearyltrimethylammonium chloride, distearyldimethylammonium chloride, lauryldimethylammonium chloride, lauryldimethylbenzylammonium chloride and tricetylmethylammonium chloride. Other useful cationic surfactants are quaternised protein hydrolysates.

As well as non-ionic organic thickeners with properties similar to wax and non-ionic surfactants, the colouring preparation can include the usual cosmetic cationic resins. Particularly preferred are Polyquaternium-6 (poly(dimethyldiallylammonium chloride)), Polyquaternium-7 (diethyldiallylammonium chloride/acrylamide copolymer), Polyquaternium-10 (cationic cellulose), Polyquaternium-11 (diethyl sulphate of N,N-dimethylaminoethylmethacrylic acid/PVP copolymer), Polyquaternium-22, Polyquaternium-35, Polyquaternium-37 (trimethylaminoethyl methacrylate chloride polymer) and Polyquaternium-113, either alone or in mixtures thereof. The total amount of said cationic resins in the preparation can range from about 0.1 to 6% by weight.

The composition according to the invention can be applied to the hair by the following methods, for example:
1—The composition is mixed with an activator immediately before dyeing the hair, and a sufficient amount of ready-to-use dye mixture, generally about 60 to 200 grams, depending on the thickness and amount of the hair, is then applied to the hair.
 The mixture is left on the hair for 5 to 60 minutes at the temperature of 5 to 50° C., preferably for 35 minutes at 30° C.; the hair is then rinsed with water and dried. If necessary, the hair is washed with shampoo after rinsing and optionally rinsed again with a weak organic acid, such as an aqueous solution of tartaric acid. The hair is then dried.
2—The dye is applied directly to the hair and left for 5 to 60 minutes at a temperature ranging from 5 to 50° C., preferably for 35 minutes at 30° C.; the hair is then rinsed with water and dried. The dye can be applied for several consecutive days until the desired colour depth is reached. In this case the oxygen in the air acts as activator (progressive dye).
3—The dye is applied directly to the hair and then dried without rinsing. The dye can be applied for several consecutive days until the desired depth is reached. Once again, the oxygen in the air acts as activator (progressive dye).

The following examples further illustrate the invention.

EXAMPLES

The ingredients listed in the examples are named according to the INCI nomenclature (European Community Decision 2006/257/EC as amended—International Nomenclature of Cosmetic Ingredients).

Table 1 shows the formulas of the activators used for the examples below. Formulas A1, A2, A3 and A4 represent the different strengths of the activators, namely 40 volumes, 30 volumes, 20 volumes and 10 volumes respectively.

TABLE 1

| | Activators | | | |
|---|---|---|---|---|
| INGREDIENTS | A1 % | A2 % | A3 % | A4 % |
| AQUA (WATER) | q.s. for 100 | q.s. for 100 | q.s. for 100 | q.s. for 100 |
| HYDROGEN PEROXIDE | 12 | 9 | 6 | 3 |
| CETEARYL ALCOHOL | 3 | 3 | 3 | 3 |
| CETEARETH-20 | 0.6 | 0.6 | 0.6 | 0.6 |
| PHOSPHORIC ACID | 0.1 | 0.1 | 0.1 | 0.1 |
| SODIUM STANNATE | 0.2 | 0.2 | 0.2 | 0.2 |
| SODIUM LAURETH SULPHATE | 0.1 | 0.1 | 0.1 | 0.1 |
| PROPYLENE GLYCOL | 0.5 | 0.5 | 0.5 | 0.5 |
| DISODIUM PYROPHOSPHATE | 0.1 | 0.1 | 0.1 | 0.1 |
| DIMETHICONE | 0.1 | 0.1 | 0.1 | 0.1 |
| PEG-40 CASTOR OIL | 0.5 | 0.5 | 0.5 | 0.5 |
| PENTASODIUM PENTETATE | 0.1 | 0.1 | 0.1 | 0.1 |
| ETIDRONIC ACID | 0.1 | 0.1 | 0.1 | 0.1 |

Table 2 shows the cream formulas of the hair-colouring preparations used in the subsequent lightening and cosmetic colour removal tests.

The formulas used for the lightening test do not contain dyes, and F1* and F1* are the formulas according to the invention.

The amounts of the ingredients are expressed as a percentage by weight of the total weight of the composition, and the percentage of alkaliser used is that required on each occasion to obtain a pH greater than 8.

TABLE 2

| Hair-colouring preparations for lightening test | | | | | | | | | | | | |
|---|---|---|---|---|---|---|---|---|---|---|---|---|
| | F1* | F2 | F3 | F4 | F5 | F6 | F7 | F8 | F9 | F10 | F11* | F12 |
| AQUA (WATER) | q.s. for 100 | q.s. for 100 | q.s. for 100 | q.s. for 100 | q.s. for 100 | q.s. for 100 | q.s. for 100 | q.s. for 100 | q.s. for 100 | q.s. for 100 | q.s. for 100 | q.s. for 100 |
| CETEARYL ALCOHOL | 20 | 20 | 20 | 20 | 20 | 20 | 20 | 20 | 20 | 20 | 20 | 20 |
| ISOPROPANOLAMINE (MIPA) | 10 | 10 | — | — | — | — | — | — | 10 | 10 | 10 | — |

TABLE 2-continued

Hair-colouring preparations for lightening test

| | F1* | F2 | F3 | F4 | F5 | F6 | F7 | F8 | F9 | F10 | F11* | F12 |
|---|---|---|---|---|---|---|---|---|---|---|---|---|
| DIISOSTEARYL MALATE | 2 | — | 2 | 2 | 2 | 2 | 2 | 2 | — | — | — | 2 |
| TRIETHANOLAMINE (TEA) | — | — | 10 | — | — | — | — | — | — | — | — | — |
| AMINOMETHYLPROPANOL (AMP) | — | — | — | 10 | — | — | — | — | — | — | — | — |
| DIMETHYLAMINO METHYLPROPANOL(DMAMP) | — | — | — | — | 10 | — | — | — | — | — | — | — |
| AMMONIUM CARBONATE | — | — | — | — | — | 5 | — | — | — | — | — | — |
| ETHANOLAMINE (MEA) | — | — | — | — | — | — | — | — | 10 | — | — | — |
| MALIC ACID | — | — | — | — | — | — | — | — | — | 2 | — | — |
| ISOSTEARYL LACTATE | — | — | — | — | — | — | — | — | — | — | 2 | — |
| DI-C12-13 ALKYL MALATE | — | — | — | — | — | — | — | — | — | — | 2 | — |
| AMMONIA | — | — | — | — | — | — | — | — | — | — | — | 2 |
| ARGININE | — | — | — | — | — | — | 10 | — | — | — | — | — |
| LAURETH-3 | 3 | 1.7 | 3 | 3 | 3 | 3 | 3 | 3 | 3 | 3 | 3 | 3 |
| SODIUM LAURETH SULPHATE | 1.65 | 1.02 | 1.65 | 1.65 | 1.65 | 1.65 | 1.65 | 1.65 | 1.65 | 1.65 | 1.65 | 1.65 |
| OLETH-5 PHOSPHATE | 1.02 | 1.02 | 1.02 | 1.02 | 1.02 | 1.02 | 1.02 | 1.02 | 1.02 | 1.02 | 1.02 | 1.02 |
| DIOLEYL PHOSPHATE | 0.98 | 0.98 | 0.98 | 0.98 | 0.98 | 0.98 | 0.98 | 0.98 | 0.98 | 0.98 | 0.98 | 0.98 |
| SODIUM LAURYL SULPHATE | 0.9 | 0.9 | 0.9 | 0.9 | 0.9 | 0.9 | 0.9 | 0.9 | 0.9 | 0.9 | 0.9 | 0.9 |
| GLYCERYL STEARATE SE | 0.75 | 0.75 | 0.75 | 0.75 | 0.75 | 0.75 | 0.75 | 0.75 | 0.75 | 0.75 | 0.75 | 0.75 |
| PARFUM (FRAGRANCE) | 0.6 | 0.6 | 0.6 | 0.6 | 0.6 | 0.6 | 0.6 | 0.6 | 0.6 | 0.6 | 0.6 | 0.6 |
| CERA ALBA (BEESWAX) | 0.5 | 0.5 | 0.5 | 0.5 | 0.5 | 0.5 | 0.5 | 0.5 | 0.5 | 0.5 | 0.5 | 0.5 |
| SODIUM SULPHATE | 0.5 | 0.5 | 0.5 | 0.5 | 0.5 | 0.5 | 0.5 | 0.5 | 0.5 | 0.5 | 0.5 | 0.5 |
| SODIUM SULPHITE | 0.5 | 0.5 | 0.5 | 0.5 | 0.5 | 0.5 | 0.5 | 0.5 | 0.5 | 0.5 | 0.5 | 0.5 |
| EDTA | 0.3 | 0.3 | 0.3 | 0.3 | 0.3 | 0.3 | 0.3 | 0.3 | 0.3 | 0.3 | 0.3 | 0.3 |
| ERYTHORBIC ACID | 0.2 | 0.2 | 0.2 | 0.2 | 0.2 | 0.2 | 0.2 | 0.2 | 0.2 | 0.2 | 0.2 | 0.2 |
| *LIMNANTHES ALBA* (MEADOWFOAM) SEED OIL | 0.2 | 0.2 | 0.2 | 0.2 | 0.2 | 0.2 | 0.2 | 0.2 | 0.2 | 0.2 | 0.2 | 0.2 |

Table 3 shows the cream formulas of the hair-colouring preparations used in the subsequent tests relating to hair damage (evaluated in terms of combability, elasticity, shine and integrity) and coverage of white hair.

The formulas in that case contain dyes, and F13* is the formula according to the invention.

The amounts of the ingredients are expressed as a percentage by weight of the total weight of the composition, and the percentage of alkaliser used is that required on each occasion to obtain a pH greater than 8.

TABLE 3

Hair-colouring preparations for combability, elasticity, shine and integrity test

| | F13* | F14 | F15 | F16 | F17 | F18 | F19 | F20 | F21 | F22 | F23 |
|---|---|---|---|---|---|---|---|---|---|---|---|
| AQUA (WATER) | q.s. for 100 | q.s. for 100 | q.s. for 100 | q.s. for 100 | q.s. for 100 | q.s. for 100 | q.s. for 100 | q.s. for 100 | q.s. for 100 | q.s. for 100 | q.s. for 100 |
| CETEARYL ALCOHOL | 20 | 20 | 20 | 20 | 20 | 20 | 20 | 20 | 20 | 20 | 20 |
| ISOPROPANOLAMINE | 10 | 10 | — | — | — | — | — | 10 | 10 | — | — |
| DIISOSTEARYL MALATE | 2 | — | 2 | 2 | 2 | 2 | 2 | — | — | 2 | — |
| TRIETHANOLAMINE (TEA) | — | — | 10 | — | — | — | — | — | — | — | — |
| AMINOMETHYLPROPANOL (AMP) | — | — | — | 10 | — | — | — | — | — | — | — |
| DIMETHYLAMINO METHYLPROPANOL(DMAMP) | — | — | — | — | 10 | — | — | — | — | — | — |
| AMMONIUM CARBONATE | — | — | — | — | — | 5 | — | — | — | — | — |
| ETHANOLAMINE (MEA) | — | — | — | — | — | — | 10 | — | — | — | — |
| MALIC ACID | — | — | — | — | — | — | — | 2 | — | — | — |
| ISOSTEARYL LACTATE | — | — | — | — | — | — | — | — | 2 | — | — |
| AMMONIA | — | — | — | — | — | — | — | — | — | 2 | — |
| ARGININE | — | — | — | — | — | — | — | — | — | — | 10 |
| LAURETH-3 | 3 | 3 | 3 | 3 | 3 | 3 | 3 | 3 | 3 | 3 | 3 |
| SODIUM LAURETH SULPHATE | 1.65 | 1.65 | 1.65 | 1.65 | 1.65 | 1.65 | 1.65 | 1.65 | 1.65 | 1.65 | 1.65 |
| OLETH-5 PHOSPHATE | 1.02 | 1.02 | 1.02 | 1.02 | 1.02 | 1.02 | 1.02 | 1.02 | 1.02 | 1.02 | 1.02 |
| DIOLEYL PHOSPHATE | 0.98 | 0.98 | 0.98 | 0.98 | 0.98 | 0.98 | 0.98 | 0.98 | 0.98 | 0.98 | 0.98 |
| SODIUM LAURYL SULPHATE | 0.9 | 0.9 | 0.9 | 0.9 | 0.9 | 0.9 | 0.9 | 0.9 | 0.9 | 0.9 | 0.9 |
| GLYCERYL STEARATE SE | 0.75 | 0.75 | 0.75 | 0.75 | 0.75 | 0.75 | 0.75 | 0.75 | 0.75 | 0.75 | 0.75 |
| PEG-90-GLYCERYL ISOSTEARATE | — | — | — | — | — | — | — | — | — | — | 1 |
| PARFUM (FRAGRANCE) | 0.6 | 0.6 | 0.6 | 0.6 | 0.6 | 0.6 | 0.6 | 0.6 | 0.6 | 0.6 | 0.6 |
| CERA ALBA (BEESWAX) | 0.5 | 0.5 | 0.5 | 0.5 | 0.5 | 0.5 | 0.5 | 0.5 | 0.5 | 0.5 | 0.5 |
| SODIUM SULPHATE | 0.5 | 0.5 | 0.5 | 0.5 | 0.5 | 0.5 | 0.5 | 0.5 | 0.5 | 0.5 | 0.5 |

TABLE 3-continued

Hair-colouring preparations for combability, elasticity, shine and integrity test

| | F13* | F14 | F15 | F16 | F17 | F18 | F19 | F20 | F21 | F22 | F23 |
|---|---|---|---|---|---|---|---|---|---|---|---|
| SODIUM SULPHITE | 0.5 | 0.5 | 0.5 | 0.5 | 0.5 | 0.5 | 0.5 | 0.5 | 0.5 | 0.5 | 0.5 |
| EDTA | 0.3 | 0.3 | 0.3 | 0.3 | 0.3 | 0.3 | 0.3 | 0.3 | 0.3 | 0.3 | 0.3 |
| ERYTHORBIC ACID | 0.2 | 0.2 | 0.2 | 0.2 | 0.2 | 0.2 | 0.2 | 0.2 | 0.2 | 0.2 | 0.2 |
| *LIMNANTHES ALBA* SEED OIL (*LIMNANTHES ALBA* (MEADOWFOAM) SEED OIL) | 0.2 | 0.2 | 0.2 | 0.2 | 0.2 | 0.2 | 0.2 | 0.2 | 0.2 | 0.2 | 0.2 |
| TOLUENE-2,5-DIAMINE SULPHATE | 1.66 | 1.66 | 1.66 | 1.66 | 1.66 | 1.66 | 1.66 | 1.66 | 1.66 | 1.66 | 1.66 |
| 2-METHYLRESORCINOL | 0.44 | 0.44 | 0.44 | 0.44 | 0.44 | 0.44 | 0.44 | 0.44 | 0.44 | 0.44 | 0.44 |
| RESORCINOL | 0.28 | 0.28 | 0.28 | 0.28 | 0.28 | 0.28 | 0.28 | 0.28 | 0.28 | 0.28 | 0.28 |
| M-AMINOPHENOL | 0.15 | 0.15 | 0.15 | 0.15 | 0.15 | 0.15 | 0.15 | 0.15 | 0.15 | 0.15 | 0.15 |
| 2,4-DIAMINOPHENOXYETHANOL HCL | 0.01 | 0.01 | 0.01 | 0.01 | 0.01 | 0.01 | 0.01 | 0.01 | 0.01 | 0.01 | 0.01 |

Tables 4 and 5 show other examples of compositions according to the invention in gel and liquid form, namely F24* and F25* respectively.

TABLE 4

Dye according to the invention, in gel form.

| Ingredients (INCI) | F24* |
|---|---|
| AQUA | q.s. to 100 |
| PROPYLENE GLYCOL | 7 |
| HYDROXYETHYLCELLULOSE | 2 |
| CARBOMER | 1 |
| ACRYLATES/METHACRYLAMIDE COPOLYMER | 0.3 |
| ISOPROPANOLAMINE (MIPA) | 9 |
| DIISOSTEARYL MALATE | 2 |
| SODIUM HYDROXIDE | 1 |
| PARFUM (FRAGRANCE) | 0.6 |
| SODIUM SULPHITE | 0.5 |
| ERYTHORBIC ACID | 0.3 |
| EDTA | 0.2 |
| TOLUENE-2,5-DIAMINE SULPHATE | 2.14 |
| 4-CHLORORESORCINOL | 1.36 |
| P-AMINOPHENOL | 0.73 |
| M-AMINOPHENOL | 0.70 |
| 2,4-DIAMINOPHENOXYETHANOL HCL | 0.07 |
| 2-AMINO-3-HYDROXYPYRIDINE | 0.03 |

TABLE 5

Dye according to the invention, in liquid form.

| | F25* |
|---|---|
| AQUA (WATER) | q.s. for 100 |
| ALCOHOL DENAT. | 12 |
| OLEIC ACID | 12 |
| PROPYLENE GLYCOL | 10 |
| LAURETH-2 | 8 |
| LAURETH-3 | 4 |
| OLEYL ALCOHOL | 3.5 |
| ISOPROPANOLAMINE (MIPA) | 6 |
| SODIUM LAURETH SULPHATE | 3 |
| POTASSIUM HYDROXIDE | 2 |
| DIISOSTEARYL MALATE | 1 |
| PARFUM (FRAGRANCE) | 0.7 |
| CETRIMONIUM CHLORIDE | 0.5 |
| P-PHENYLENEDIAMINE | 0.4 |
| ERYTHORBIC ACID | 0.4 |
| SODIUM SULPHITE | 0.4 |
| EDTA | 0.3 |
| RESORCINOL | 0.3 |
| 2-METHYLRESORCINOL | 0.12 |
| M-AMINOPHENOL | 0.07 |
| P-AMINOPHENOL | 0.066 |
| 2,4-DIAMINOPHENOXYETHANOL HCL | 0.018 |

Test 1: Shine

The SAMBA Hair System instrument made by Bossanova Technologies was used to conduct this test. The formula used to evaluate differences in shine was Reich-Robbins (Light scattering and shine measurements of human hair: A sensitive probe of the hair surface. J. Soc. Cosmet. Chem., 44, 221-234. July/August 1993).

The compositions listed in table 3 were mixed with activator A3 listed in table 1 at the ratio of 1:2.

5 g of the resulting mixtures was applied to locks of level 5 natural hair; after 35 minutes at a temperature of 30° C., the locks were rinsed with water and dried. The application was repeated 5 times before conducting the shine measurement.

Table 6 shows the values expressed as percentage differences compared with formula F19 containing monoethanolamine. Positive values indicate a better shine.

TABLE 6

Shine test

| | F13* | F14 | F15 | F16 | F17 | F18 | F20 | F21 | F22 | F23 |
|---|---|---|---|---|---|---|---|---|---|---|
| Reich-Robbins % Vs F19 | +150% | +135% | +125% | +75% | +95% | 50% | +131% | +122% | +146% | +148% |

F13* according to the invention gives rise to a better shine (+150%) than F19 containing monoethanolamine. The result is comparable with that obtained with ammonia (F22) or using the arginine+PEG-90 glyceryl isostearate alkalising system (F23). However, Formula F14 containing MIPA without diisostearyl malate also has an excellent profile compared with the dye containing MEA, and the addition of non-esterified malic acid (formula F20) does not generate any improvements in terms of shine.

Test 2: Combability

The combability test was conducted with a DIA-STRON MTT175 dynamometer, used to evaluate the work required to comb the locks of hair. The hair used in said test was hair damaged by a bleaching treatment. For this purpose, all compositions, from F13* to F23, were mixed individually with composition A2 at the ratio of 1:1.5, and 5 g of each resulting mixture was applied to the bleached locks. After 35 minutes at a temperature of 30° C. the locks were rinsed with water, dried, and introduced into the dynamometer for measurement.

The test results are set out in table 7, expressed as percentage differences compared with bleached hair. The percentage reduction indicates a reduction in the work required to comb the hair due to lower friction of the comb on the hair fibers. Thus the greater the percentage reduction, the better the combability.

TABLE 7

Dynamometric combability test:

| Formulation applied to bleached hair | % reduction compared with bleached hair |
|---|---|
| F13* | 58% |
| F14 | 51% |
| F15 | 33% |
| F16 | 26% |
| F17 | 28% |
| F18 | 10% |
| F19 | 25% |
| F20 | 48% |
| F21 | 45% |
| F22 | 48% |
| F23 | 53% |

The data demonstrate that the hair-colouring preparation according to the invention (F13*) leaves the hair more manageable and combable than formula F19, which contains MEA. The result is comparable with that obtained with ammonia (F22) or using the arginine+PEG-90 glyceryl isostearate alkalising system (F23). Once again formula F14, containing MIPA without diisostearyl malate, has an excellent profile compared with the preparation containing MEA.

Test 3: Tensile Properties

A DIA-STRON MTT670 dynamometer was used to evaluate the tensile properties of the hair. The evaluation was conducted on locks of natural blonde hair, which were dyed with the formulations listed in table 3 mixed with activator A4 at the ratio of 1:1. The application was conducted 5 consecutive times by the method described in test 1.

The reference parameter is the modulus of elasticity (Young's Modulus). The higher said parameter, the better the health (elasticity) of the hair. Table 8 shows the percentage values obtained for untreated natural blonde hair. The greater the reduction in the modulus of elasticity compared with natural hair, the greater the hair damage caused by the hair dye applied.

TABLE 8

Dynamometric elasticity test

| Formula | % variation in modulus of elasticity |
|---|---|
| F13* | −2% |
| F14 | −8% |
| F15 | −15% |
| F16 | −14% |
| F17 | −13% |
| F18 | −40% |
| F19 | −25% |
| F20 | −9% |
| F21 | −8.5% |
| F22 | −6% |
| F23 | +5% |

This example demonstrates that formulation F13* according to the invention damages the hair less after 5 consecutive treatments than F19 containing monoethanolamine. F13* performed better than all the compositions reported apart from the preparation containing arginine (F23) which, however, presents the drawback of not lightening the hair (as will be demonstrated below).

Test 4: Integrity

"Integrity" means the extent of erosion of the keratin fiber. Detailed images of the hair cuticles can be obtained with a scanning electron microscope (SEM). Image-J software provides a method of measuring the distance between cuticles. The shorter the cuticles, the healthier the hair. On damaged hair, the cuticle has been removed (eroded) by the treatment (such as a dye), and the distance between the remaining layers of cuticle is longer. Table 9 shows the mean data from numerous measurements, expressed in μm. For this purpose, all the compositions from F13* to F23 were mixed individually with composition A4 at the ratio of 1:2 and applied to natural blonde locks. The application was conducted 5 consecutive times by the method described in test 1.

TABLE 9

Cuticle integrity evaluation.

| Formula | Mean distance between cuticles (μm) |
|---|---|
| F13* | 8.15 |
| F14 | 8.65 |
| F15 | 9.3 |
| F16 | 10.2 |
| F17 | 9.85 |
| F18 | 12.5 |
| F19 | 11.2 |
| F20 | 8.76 |
| F21 | 8.91 |
| F22 | 8.23 |
| F23 | 8.17 |

Composition F13* according to the invention proved the best in terms of preventing cuticle erosion. The result is comparable with that of composition F23 containing arginine (which does not, however, lighten the hair), and slightly better than that of formula F22 containing ammonia (which, however, has an unpleasant odour). However, formula F14 containing MIPA without diisostearyl malate has a good profile, better than that of the formula containing MEA (F19). The addition of non-esterified malic acid (F20) did not produce any improvement.

Test 5: Lightening

Locks of natural dark brown hair were used for this test. The compositions used were those listed in table 2 mixed with activator A1 at the ratio of 1:2, applied to the locks for 35 minutes and then rinsed under running water and dried.

Lightening was evaluated by visual inspection conducted by experts in the field. The value shown in table 10 indicates a difference in lightening levels between an untreated lock of natural dark brown hair and a lock treated with the various compositions. A higher value indicates a greater level of lightening. For example, 4 levels of lightening indicate a change from dark brown to medium blonde.

TABLE 10

Lightening evaluation

| Formula | Difference in lightening |
|---|---|
| F1* | 3.8 |
| F2 | 3.5 |
| F3 | 0.5 |
| F4 | 0.6 |
| F5 | 0.3 |
| F6 | 4.5 |
| F7 | 0.2 |
| F8 | 3.6 |
| F9 | 3.5 |
| F10 | 3.5 |
| F11* | 3.7 |
| F12 | 4 |

Compositions F1* and F11* according to the invention generated better lightening than any of the compositions listed in table 2, except for F6 containing ammonium carbonate and F12 containing ammonia. As already stated, however, compositions containing ammonia emit an unpleasant odour poorly tolerated by consumers, while compositions containing ammonium carbonate tend to damage the hair badly, as found in the preceding tests.

Both F1* and F11* (according to the invention) generate slightly greater lightening than that obtained with MEA (F8).

However, composition F2 containing MIPA without malic acid diester lightens the hair slightly less than formula F8 containing MEA.

Malic acid diester therefore has the effect of enhancing lightening if combined with MIPA.

The result produced by formula F9 demonstrates that the presence of non-esterified malic acid does not improve the lightening generated by MIPA.

The result generated by formula F10 demonstrates that the presence of isostearyl lactate, another emollient commonly used in the cosmetic industry, a lactic acid monoester, has no effect on the lightening generated by MIPA.

Compositions F1* and F11* according to the invention present a much higher value of lightening power than composition F7 containing arginine. F7 is unable to lighten natural hair.

Test 6: Coverage of White Hair 6 models with different percentages of white hair were used for this test. The compositions used were F13*, F14 and F19 mixed with activator A4 at the ratio of 1:1 and applied to the roots of the model's hair (presenting white hair regrowth) for 35 minutes, then rinsed under running water and dried.

White hair coverage was evaluated by visual inspection by 5 experts in the field. The evaluation scale comprised a score of 0 to 4 as follows:
 0: No coverage
 1: Slight coverage
 2: Fairly good coverage
 3: Good coverage
 4: Excellent coverage

TABLE 11

Evaluation of white hair coverage

| Formula | Mean evaluation |
|---|---|
| F13* | 3.2 |
| F14 | 2.6 |
| F19 | 1.8 |

Composition F13* according to the invention generated the best coverage of white hair, and the difference between F13* and F19 (preparation containing MEA as alkalising agent) was particularly significant.

Test 7: Removal of Cosmetic Colour

The artificially coloured locks used for this test were prepared with homogenised 100% white hair to which the EOC CUBE 5.0 dye made by Alfaparf Milan was applied, mixed at the ratio of 1:1.5 with Oxid'o Alfaparf, 20 Vol, processing time 35 minutes.

Compositions F1*, F2 and F8 were mixed with activator A1 at the ratio of 1:2. Said mixture was applied to the artificially coloured locks, left to process for 35 minutes, and then rinsed and dried.

Cosmetic colour removal was evaluated by visual inspection conducted by 5 experts in the field. The value shown in table 12 indicates the difference between an artificially coloured lock (comparator) and a lock treated with the various compositions. The evaluation scale comprised a score of 0 to 4 as follows:
 0: No removal
 1: Slight removal
 2: Fairly good removal
 3: Good removal
 4: Excellent removal

TABLE 12

Evaluation of cosmetic colour removal

| Formula | Mean evaluation |
|---|---|
| F1* | 1.6 |
| F2 | 1.4 |
| F8 | 0.6 |

Composition F1* according to the invention generated the best removal of cosmetic colour, and the difference between F1* and F8 (containing MEA) was particularly significant.

The invention claimed is:

1. Hair-colouring compositions comprising an oxidative dye and an alkalising agent consisting of isopropanolamine and a malic acid diester.

2. Compositions according to claim 1 wherein the malic acid diester is a di-C12-13 alkyl malate.

3. Compositions according to claim 1 wherein the malic acid diester is diisostearyl malate.

4. Compositions according to claim 1 comprising 0.1 to 10% by weight of isopropanolamine and 0.1 to 20% by weight of malic acid diester.

5. Compositions according to claim 1 comprising two or more components, at least one of which is an activator, to be mixed before use.

6. Compositions according to claim 1 in cream, gel, foam, liquid or solid form.

7. Compositions according to claim 1 further comprising a direct dye.

* * * * *